United States Patent [19]

Müller et al.

[11] Patent Number: 5,342,881
[45] Date of Patent: Aug. 30, 1994

[54] PROCESS FOR THE STANDARDIZATION AND STABILIZATION OF ORGANIC POLYISOCYANATES AND THE STABLE PRODUCTS OF THIS PROCESS

[75] Inventors: Hanns-Peter Müller, Odenthal; Hans-Joachim Scholl, Cologne; Manfred Kapps, Bergisch Gladbach, all of Fed. Rep. of Germany

[73] Assignee: Bayer Aktiengesellschaft, Leverkusen, Fed. Rep. of Germany

[21] Appl. No.: 65,251

[22] Filed: May 20, 1993

[30] Foreign Application Priority Data

May 27, 1992 [DE] Fed. Rep. of Germany ....... 4217525

[51] Int. Cl.$^5$ .................. C08K 5/54; C08K 5/56; C08J 3/00
[52] U.S. Cl. ................... 524/700; 124/730; 528/66; 528/73; 528/87; 528/100; 521/121; 521/122; 521/156; 521/161
[58] Field of Search ............ 521/121, 122, 161, 156; 528/73, 66, 87, 100; 524/700, 730

[56] References Cited

U.S. PATENT DOCUMENTS

| | | | |
|---|---|---|---|
| 4,014,935 | 3/1977 | Ibbotson | 260/566 R |
| 5,021,536 | 6/1991 | Müller et al. | 528/73 |
| 5,173,559 | 12/1992 | Müller et al. | 528/44 |

FOREIGN PATENT DOCUMENTS

| | | |
|---|---|---|
| 2036538 | 9/1991 | Canada . |
| 2037085 | 9/1991 | Canada . |
| 166264 | 1/1986 | European Pat. Off. . |
| 374932 | 6/1990 | European Pat. Off. . |
| 285593 | 12/1990 | Fed. Rep. of Germany . |
| 1080717 | 8/1967 | United Kingdom . |

OTHER PUBLICATIONS

Chem. Soc. Rev. 3 (1974), p. 209 ff.

*Primary Examiner*—John Kight, III
*Assistant Examiner*—Duc Truong
*Attorney, Agent, or Firm*—Joseph C. Gil; Lyndanne M. Whalen

[57] ABSTRACT

A new process for the standardization and stabilization with simultaneous increase of reactivity of organic polyisocyanates and the polyisocyanates produced by this process. A polyisocyanate is mixed with compounds having at least one epoxide group which are represented by a specified formula. This mixture is then stabilized with a silylating agent and/or alkylating agent represented by specified formula. The polyisocyanate/epoxide mixture may optionally be heated before the stabilizing agents are added. These polyisocyanates are useful in the production of polyisocyanate addition products.

15 Claims, No Drawings

PROCESS FOR THE STANDARDIZATION AND STABILIZATION OF ORGANIC POLYISOCYANATES AND THE STABLE PRODUCTS OF THIS PROCESS

BACKGROUND OF THE INVENTION

The present invention relates to a new process for the standardization and stabilization of organic polyisocyanates, to the polyisocyanates obtained by this process and to the use of those stable polyisocyanates to produce polyisocyanate addition products.

The nature and amount of impurities in polyisocyanates are determined by the method by which they are produced. The impurities cause fluctuations in the activity of the polyisocyanate and thereby affect the products made with the polyisocyanate. Reproducible and commercial application of impurity-containing polyisocyanates is therefore difficult.

In particular, the known phosgenation products of aniline-formaldehyde condensates (crude polyisocyanate mixtures of the diphenylmethane series) contain an abundance of such impurities. According to Chem. Soc. Rev. 3 (1974), p. 209 ff., chlorine-containing impurities which always cause activity fluctuations when "labile" (so-called hydrolyzable chlorine (HC value)) are of particular concern. Narrowing the range of fluctuation by reducing the amount of these impurities to standardize and improve activity is therefore of both technical and economic importance.

DD 285,593 teaches that organic polyisocyanates are purified at 200° to 240° C. by treating with compounds containing acetamide groups or ε-caprolactam and by subsequently blowing inert gases through the polyisocyanate.

GB Pat. 1,080,717 teaches that it is possible to reduce the hydrolyzable chlorine value (HC value) by thermal treatment at 180° to 220° C.

In addition to the large expenditure of energy, such high-temperature processes are dangerous due to the extraordinary reactivity of polyisocyanates which can oligomerize with a sudden evolution of heat.

DE-OS 2,614,323 discloses a process for the conversion of polyisocyanates in which a 1,2-epoxide is used as an acid acceptor. However, this process requires use of deactivating agents such as hydrogen halides, halides of phosphorus or tin or oxyhalides of phosphorus or sulfur. The mixture of the resulting modified polyisocyanates then contains fluctuating amounts of hydrolyzable chlorine.

The known processes disclosed in EP 445,608 and EP 445,602 for the standardization of polyisocyanates are unsafe, technically demanding or produce new defects as a result of additives.

SUMMARY OF THE INVENTION

It is an object of the present invention to provide a technically simple process for the purification of organic polyisocyanates which is safe, not technically demanding and which does not require additives that affect the stability of the polyisocyanate.

It is also an object of the present invention to provide stable polyisocyanate compositions which may be made by a safe, economic process.

These and other objects which will be apparent to those skilled in the art are accomplished by mixing a) an organic polyisocyanate with b) 0.01–10 wt % epoxide represented by a specified formula and c) 0.01–1 wt % silylated acid and/or 0.01–1 wt % alkylated acid at a temperature of from about 20° to about 150° C.

DETAILED DESCRIPTION OF THE PRESENT INVENTION

The present invention is directed to a process in which a small amount of one or more compounds having at least one epoxide group is added to the technical (i.e., crude polyisocyanate) to be treated and stabilizing the resultant mixture with certain silylating agents and/or alkylating agents and to the products obtained by this process.

More specifically, the present invention provides a process for the standardization and stabilization of organic polyisocyanates in which an organic polyisocyanate is mixed at 20° C. to 150° C. with a) 0.01–10 wt %, preferably 0.1 to 2 wt %, relative to polyisocyanate, of an organic compound corresponding to formula (I) containing at least one epoxide group,

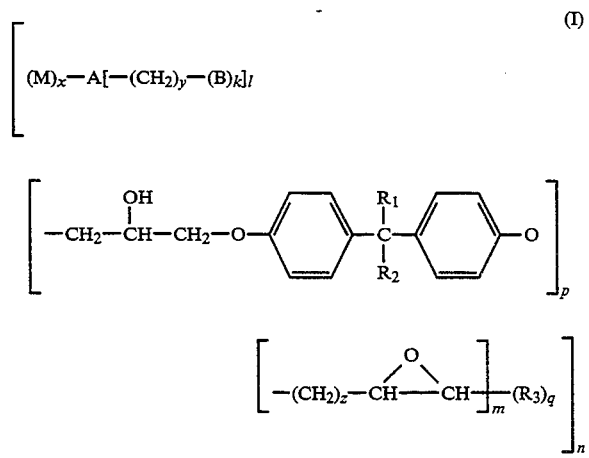

in which
x represents a number from 0 to 1,
y represents a number from 0 to 4,
z represents a number from 0 to 6,
k represents a number from 0 to 1,
l represents a number from 0 to 8,
m represents a number from 0.5 to 4,
n represents a number from 1 to 10,
p represents a number from 0 to 15,
q represents a number from 0 to 1,
A represents hydrogen, mono- or multivalent, saturated or unsaturated, cyclic or acyclic alkyl, aryl, acyl, or N-acyl groups, optionally with substituents,
B represents O, S, N,
M represents

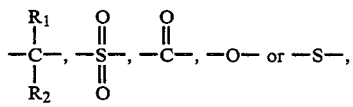

in which
$R_1$ and $R_2$ each represents hydrogen or a $C_1$ to $C_4$ alkyl group, and
$R_3$ represents hydrogen or a $C_1$-$C_4$ alkyl group and subsequently or simultaneously the reaction product is stabilized with b) 0.01 to 1 wt %, preferably 0.01 to 0.1 wt. %, relative to polyisocyanate, of a silylated acid of formula (II)

$$X-[Si(CH_3)_3]_a \qquad (II)$$

and/or an alkylated acid of formula (III)

$$X-[alkyl]_a \qquad (III)$$

in which

X represents an acidic group obtained by removal of the acidic hydrogen atoms from an acid containing a-basic oxygen with a pKa value of not more than 2, and a represents 1, 2 or 3.

Any of the known organic polyisocyanates may be used in the process of the present invention. Optionally chemically modified polyisocyanates or polyisocyanate mixtures of the diphenylmethane series are preferably used.

As compounds of formula (II), trifluoromethanesulfonic acid trimethylsilyl ester or phosphoric acid tris(-trimethylsilyl ester) are preferably used.

As compounds of formula (III), benzenesulfonic acid methyl ester, methanesulfonic acid methyl ester, trifluoromethanesulfonic acid methyl ester or toluenesulfonic acid methyl ester are preferably used.

The stabilizers (II) and (III) can be used alone or together in mixtures of any desired proportions.

The polyisocyanates purified by the process of the present invention are preferably used as starting materials for the production of plastics.

The present invention also provides polyisocyanates which are useful as starting materials in the production of polyurethane plastics in the isocyanate polyaddition process, in the production of modified polyisocyanates, in the production of polyisocyanurate plastics and in particular in the production of polyurethane foamed plastics.

Starting materials for the process of the present invention include any of the known organic polyisocyanates. Specific examples of suitable polyisocyanates include: (cyclo)aliphatic diisocyanates such as 1,6-diisocyanatohexane (HDI), 1-isocyanato-3,3,5-trimethyl-5-isocyanatomethyl-cyclohexane (IPDI), 4,4'-diisocyanatodicyclohexylmethane (HMDI) and any desired mixtures of such aliphatic diisocyanates; aromatic diisocyanates such as 2,4- and/or 2,6-diisocyanatotoluene (TDI); modified polyisocyanates; and reaction mixtures such as those obtained during the trimerization of a part of the isocyanate groups of HDI, IPDI or mixtures of HDI and IPDI for the purpose of production of the corresponding polyisocyanates containing isocyanurate groups, and that consist essentially of the starting diisocyanates mentioned and the polyisocyanates having isocyanurate groups formed.

Polyisocyanates or polyisocyanate mixtures of the diphenylmethane series which are optionally chemically modified are particularly preferred starting materials for the process of the present invention. These include, for example, the crude phosgenation products of aniline/formaldehyde condensates ("crude MDI"); and distillate fractions obtained from these crude mixtures. Examples of such distillate fractions are polyisocyanates or polyisocyanate mixtures composed of from 40 to 100 wt % diisocyanatodiphenylmethane isomers and from 0 to 60 wt % higher than difunctional polyisocyanates of the diphenylmethane series, particularly mixtures in which the diisocyanato-diphenylmethane isomers are from 40 to 100 wt %, (preferably 40 to 80 wt %) of 4,4'-diisocyanatodiphenylmethane and the rest is 2,4'-diisocyanatodiphenylmethane and optionally 2,2'-diisocyanatodiphenylmethane with the proportion of the 2,2'-diisocyanate being up to 8 wt %, relative to the weight of the diisocyanates.

The polyisocyanates or polyisocyanate mixtures mentioned can also be used in chemically modified form. As used herein, "chemical modification" means urethanization, carbodiimidization, dimerization or trimerization of a part of the isocyanate groups. Suitable urethanized starting compounds include the reaction products of a polyisocyanate or polyisocyanate mixture with insufficient amounts of polyhydric alcohol (polypropylene glycols of a maximum molecular weight of 700) formed while maintaining an NCO/OH equivalent ratio of 10:1 to 10:3. Carbodiimidization products useful in the process of the present invention include derivatives of the polyisocyanates or polyisocyanate mixtures described above which contain carbodiimide groups and/or uretonimine groups, that have been produced by carbodiimidization of from 5 to 30 wt % of the isocyanate groups with the aid of known carbodiimidization catalysts in accordance with known carbodiimidization techniques. Suitable dimerization and/or trimerization products include derivatives of known polyisocyanates or polyisocyanate mixtures having from 10 to 30% (based on isocyanate groups in the starting material) uretdione and/or isocyanurate groups that have been produced by known dimerization and/or trimerization techniques. Any mixtures of the chemically modified polyisocyanates or polyisocyanate mixtures can also be used in the process of the present invention.

The most preferred polyisocyanates used in the process of the present invention are the crude polyisocyanate mixtures of the diphenylmethane series with a viscosity at 24° C. of from 10 to 800 mPa.s, preferably 15 to 400 mPa.s. These most preferred polyisocyanate mixtures generally have a hydrolyzable chlorine content (HC value) of from 0.01 to 0.2 wt %, preferably 0.02 to 0.1 wt %.

In the process of the present invention, the starting polyisocyanate is treated with from 0.01 to 10 wt %, preferably from 0.1 to 2 wt %, of at least one compound represented by the formula (I), which compound has at least one epoxide group:

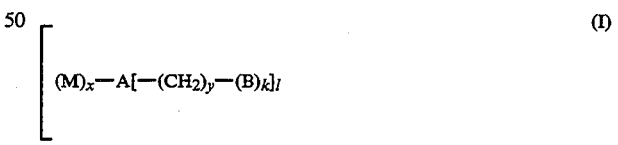

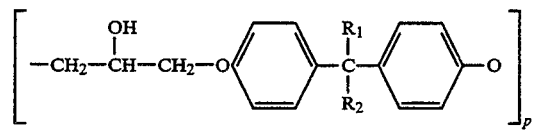

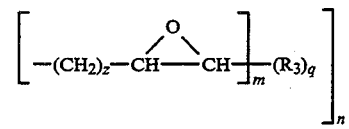

in which x represents a number from 0 to 1,
y represents a number from 0 to 4,
z represents a number from 0 to 6,
k represents a number from 0 to 1,
l represents a number from 0 to 8,
m represents a number from 0.5 to 4,
n represents a number from 1 to 10,
p represents a number from 0 to 15,
q represents a number from 0 to 1,
A represents H, mono- or multivalent, saturated or unsaturated, cyclic or acyclic alkyl, aryl, acyl, or N-acyl groups, optionally with substituents,
B represents O, S or N,
M represents

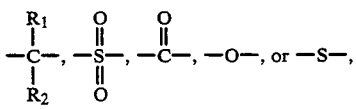

in which
R$_1$ and R$_2$ each represents hydrogen or a C$_1$ to C$_4$ alkyl group and
R$_3$ represents hydrogen or a C$_1$–C$_4$ alkyl group.

Specific examples of such compounds include phenoxypropylene oxide, propylene oxide, ethylene oxide, styrene oxide, butylene oxide and their mixtures. Any compounds containing at least two 1,2-epoxide groups, preferably aliphatic, cycloaliphatic, aromatic or heterocyclic compounds having at least two epoxide groups may also be employed. The polyepoxides used as component (I) preferably have 2 to 4, more preferably 2, epoxide groups per molecule and an epoxide equivalent weight of from 90 to 500, preferably from 170 to 220.

Suitable polyepoxides include polyglycidyl ethers of polyhydric phenols such as pyrocatechol, resorcinol, hydroquinone, 4,4'-dihydroxydiphenylmethane, 4,4'-dihydroxy-3,3'-dimethyldiphenylmethane, 4,4'-dihydroxydiphenylmethane, 4,4'-dihydroxydiphenylcyclohexane, 4,4'-dihydroxy-3,3'-dimethyldiphenylpropane, 4,4'-dihydroxydiphenyl, 4,4'-dihydroxydiphenylsulphone and tris(4-hydroxyphenyl)methane; chlorination and bromination products of the aforementioned diphenols; novolaks (i.e. from reaction products of mono- or polyhydric phenols with aldehydes, in particular formaldehyde, in the presence of acid catalysts); diphenols that have been obtained by esterification of 2 moles of the sodium salt of an aromatic oxycarboxylic acid with one mole of a dihalogenoalkane or dihalogenodialkylether (See, e.g., GB Pat. 1,017,612); and polyphenols that have been obtained by condensation of phenols and long-chain halogenoparaffins containing at least two halogen atoms (See, e.g., GB Pat. 1,024,288). Polyepoxide compounds based on aromatic amines and epichlorhydrin such as N-di-(2,3-epoxypropyl)aniline, N,N'-dimethyl-N,N'-diepoxy-propyl-4,4'-diaminodiphenylmethyl and N-diepoxypropyl-4-amino-phenylglycidyl ether (See, e.g., GB Patents 772,830 and 816, 923); glycidyl esters of polybasic aromatic, aliphatic and cycloaliphatic carboxylic acids such as phthalic acid diglycidyl ester, adipic acid diglycidyl ester; and glycidyl esters from reaction products from 1 mole of an aromatic or cycloaliphatic dicarboxylic acid anhydride and 0.5 mole of a diol or 1/n moles of a polyol with n hydroxyl groups or hexahydrophthalic acid diglycidyl ester, that optionally can be substituted with methyl groups may also be used in the process of the present invention.

Glycidyl ethers of polyhydric alcohols such as 1,4-butanediol, 1,4-butenediol, glycerol, trimethylolpropane, pentaerythritol and polyethylene glycols can likewise be used. Of wider interest are triglycidyl isocyanurate, N,N'-diepoxypropyloxamide, polyglycidylthioethers from polyvalent thiols (for example from bis-mercapto-methylbenzene), diglycidyltrimethylenetrisulfone and polyglycidyl ethers based on hydantoins.

Epoxidation products of multiply unsaturated compounds (such as vegetable oils and their conversion products); epoxidation products of di- and polyolefins (such as butadiene, vinylcyclohexene, 1,5-cyclooctadiene, 1,5,9-cyclododecatriene); polymers and copolymers that still contain epoxidizable double bonds (based, e.g., on polybutadiene, polyisoprene); butadiene-styrene copolymers; divinylbenzene; dicyclopentadiene; unsaturated polyesters; epoxidation products from olefins which are accessible by means of Diels-Alder addition and subsequently are converted to polyepoxides by epoxidation with per-compounds, or from compounds which contain two cyclopentene or cyclohexene rings linked via bridging atoms or groups may also be used as the epoxide component in the present invention.

Polymers of unsaturated monoepoxides, for example from methacrylic acid glycidyl ester or allyl glycidyl ether are also useful.

In the practice of the present invention, the following polyepoxide compounds or mixtures thereof are preferably used as the component represented by formula (I): propylene oxide, phenoxypropylene oxide, polyglycidyl ethers of polyhydric phenols (particularly bisphenol A); polyepoxide compounds based on aromatic amines (particularly bis(N-epoxypropyl)aniline, N,N'-dimethyl-N,N'-diepoxy-propyl-4,4'-diaminodiphenylmethane and N-diepoxypropyl-4-amino-phenyl-glycidyl ether); polyglycidyl esters from cycloaliphatic dicarboxylic acids (particularly hexahydrophthalic acid diglycidyl ester) and polyepoxides from the reaction product of n moles hexahydrophthalic anhydride and 1 mole of a polyol with n hydroxyl groups (n=a whole number from 2 to 6), in particular 3 moles hexahydrophthalic anhydride and one mole 1,1,1-trimethylolpropane; and 3,4-epoxycyclohexylethane-3,4-epoxycyclohexanecarboxylate.

Liquid polyepoxides or low-viscosity diepoxides, such as bis(N-epoxypropyl)aniline or vinylcyclohexanediepoxide may be used in particular cases to further reduce the viscosity of already liquid polyepoxides or to convert solid polyepoxides into liquid mixtures.

The stabilizer compounds employed in the present invention include those represented by formula (II):

X—[Si(CH$_3$)$_3$]$_a$      (II)

in which
X represents an acidic group such as that obtained by removal of the acidic hydrogen atoms from an acid containing a-basic oxygen with a pKa value of not more than 2, and
a represents a whole number from 1 to 3.

Preferred examples of such stabilizers are silylated sulfonic acids such as trifluoromethanesulfonic acid trimethylsilyl ester, silylated esters of phosphorus acids such as phosphoric acid tris(trimethylsilyl ester) or phosphoric acid diethyl ester trimethylsilyl ester.

Also suitable as stabilizers in the present invention include the compounds represented by formula (III)

$$X-[\text{alkyl}]_a \quad \text{(III)}$$

in which
X represents an acidic group such as that obtained by removal of the acidic hydrogen atoms from an acid containing a-basic oxygen with a pKa value of not more than 2, and
a represents a whole number from 1 to 3.

Preferred compounds represented by formula III include: sulfonic acids such as methanesulfonic acid methyl ester, trifluoromethanesulfonic acid methyl ester, toluenesulfonic acid methyl ester and benzenesulfonic acid methyl ester.

In the process of the present invention, the mixture of polyisocyanate and a compound having at least one epoxide group is preferably held for 0.5 to 5 hours at 20° to 150° C., preferably at 60° to 80° C. Subsequently, to stabilize the purified polyisocyanates, compounds represented by formula (II) and/or formula (III), optionally dissolved in the polyisocyanate used in each case, may be added, and the batch is held for a further 0.5 to 5 hours at 20° to 150° C., preferably at 60° to 100° C. It is also possible to add the compounds represented by formula (I), (II) and/or (III) to the polyisocyanate simultaneously.

The standardized and stabilized polyisocyanates can be used directly for the production of polyurethane plastics according to the isocyanate polyaddition process. It is also possible, however, to subject the polyisocyanates purified by the process of the present invention by addition of compounds of formula (I) to a modification reaction, e.g. by urethanization, trimerization, biuret formation, dimerization or allophanatization and/or carbodiimidization and subsequently to carry out the stabilization with the compounds of formula (II) and/or (III).

The polyisocyanates treated in accordance with the present invention show relatively small activity fluctuations. This may be simply illustrated on the basis of reduced HC values which are synonymous with improved activities, during comparative testing.

The present invention will be illustrated in more detail on the basis of the following examples. The indicated "HC values" refer to the content of hydrolyzable chlorine. All percentages are percentages by weight.

EXAMPLES

Starting isocyanates

Polyisocyanate 1

Crude polyisocyanate mixture of the diphenylmethane series with an NCO content of 30.9%, a viscosity of 110 mPa.s at 25° C. and an HC value of 0.068%.

Polyisocyanate 2

Crude polyisocyanate mixture of the diphenylmethane series with an NCO content of 32.2%, a viscosity of 25 mPa.s at 25° C. and an HC value of 0.021%, made up of
59% 4,4'-diisocyanatodiphenylmethane
23% 2,4'-diisocyanatodiphenylmethane
3% 2,2'-diisocyanatodiphenylmethane
15% higher-molecular homologs.

Example 1 (According to the invention)

1000 g Polyisocyanate 1 were mixed at room temperature with 20 g of an epoxy resin (glycidyl ether of bisphenol A; epoxide number=0.585) and 0.2 g p-toluenesulfonic acid methyl ester (TSE). This mixture was subsequently heated with stirring under nitrogen for 2 hours at 90° C. After cooling, an isocyanate mixture was obtained with an NCO content of 29.9%, an HC value of 0.045% and a viscosity of 145 mPa.s at 25° C.

Example 1a (Comparison)

Polyisocyanate 1 without additives was heated at 90° C. with stirring under nitrogen for 2 hours. After cooling, an isocyanate mixture was obtained with an NCO content of 30.9%, a viscosity of 110 mPa.s at 25° C. and an HC value of 0.068%. The experiment showed that as a result of heating no change occurs (See Table 1).

Example 1b (Comparison)

Polyisocyanate 1 was treated without TSE but with the epoxy resin as in Example 1. An isocyanate mixture was obtained with an NCO content of 30.0%, an HC value of 0.044% and a viscosity of 150 mPa.s at 25° C. The experiment showed that the addition of the epoxy resin reduces the HC value. The polyisocyanate was not, however, stable on storage (See Table 1).

Example 2 (According to the invention)

1000 g Polyisocyanate 1 were mixed at room temperature with 20 g of the epoxy resin from Example 1 and 0.2 g trifluoromethanesulfonic acid trimethylsilyl ester (TRIF) and subsequently heated for 2 hours at 90° C. with stirring under nitrogen. After cooling, an isocyanate mixture was obtained with an NCO content of 30.1%, an HC value of 0.043% and a viscosity of 140 mPa.s at 25° C.

Examples 1, 1a, 1b and 2 are listed in Table 1 together with Examples 3, 3a, 3b and 4 that were carried out using the materials specified in Table 1 and the procedure described in Example 1.

To test reactivity increase, the isocyanates obtained in each of the Examples were reacted in an amount corresponding to 1 mole NCO with 147 g (1 mole OH) of a polyether with an OH number of 380 started on trimethylolpropane and containing propylene oxide groups. For this purpose the polyether was preheated to 70° C., the isocyanate obtained from the specified example added, and the time until cross-linking determined.

Table 1 shows a clearly reduced HC value and an increased reactivity of the isocyanates from the Examples 1, 2, 3 and 4 (according to the invention). These good properties are also shown by the comparative Examples 1b and 3b, but these comparative isocyanates were not stable on storage.

TABLE 1

| Ex. | Composition | HC value after 2 h @ 90° C. (%) | NCO Content (%) Initial | NCO Content (%) After 2 h @ 90° C. | NCO Content (%) After 12 days @ 50° C. | Viscosity @ 25° C. (mPa·s) Initial | Viscosity @ 25° C. (mPa·s) After 2 h @ 90° C. | Viscosity @ 25° C. (mPa·s) After 12 days @ 50° C. | Crosslinking time with polyether (sec) |
|---|---|---|---|---|---|---|---|---|---|
| 1 | 1000 g polyisocyanate 1<br>20 g epoxy resin<br>0.2 g TSE | 0.045 | 30.3 | 29.9 | 29.7 | 115 | 145 | 150 | 446 |
| 1a | 1000 g Polyisocyanate I | 0.068 | 30.9 | 30.9 | 30.7 | 110 | 110 | 115 | 832 |
| 1b | 1000 g polyisocyanate 1<br>20 g epoxy resin | 0.044 | 30.3 | 30.0 | 25.1 | 115 | 150 | 3200 | — |
| 2 | 1000 g polyisocyanate 1<br>20 g epoxy resin<br>0.2 g TRIF | 0.043 | 30.3 | 30.1 | 29.9 | 115 | 140 | 145 | 514 |
| 3 | 1000 g polyisocyanate 2<br>20 g epoxy resin<br>0.2 TSE | 0.015 | 31.6 | 31.3 | 30.9 | 28 | 64 | 72 | 437 |
| 3a | 1000 g Polyisocyanate 2 | 0.021 | 32.2 | 32.2 | 32.1 | 25 | 25 | 26 | 911 |
| 3b | 1000 g polyisocyanate 2<br>20 g epoxy resin | 0.016 | 31.6 | 31.2 | 28.1 | 29 | 66 | 1050 | — |
| 4 | 1000 g polyisocyanate 2<br>20 g epoxy resin<br>0.2 g TRIF | 0.014 | 31.6 | 31.2 | 31.2 | 28 | 63 | 65 | 516 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A stabilized organic polyisocyanate composition comprising an organic polyisocyanate to which has been added

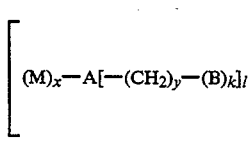  (I)

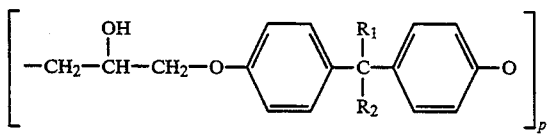

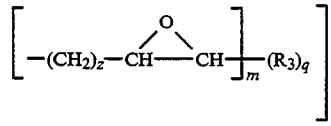

in which
x represents a number from 0 to 1,
y represents a number from 0 to 4,
z represents a number from 0 to 6,
k represents a number from 0 to 1,
l represents a number from 0 to 8,
m represents a number from 0.5 to 4,
n represents a number from 1 to 10,
p represents a number from 0 to 15,
q represents a number from 0 to 1,
A represents hydrogen, a monovalent saturated alkyl group, a multivalent saturated alkyl group, a monovalent unsaturated alkyl group, a multivalent unsaturated alkyl group, a monovalent saturated cyclic alkyl group, a multivalent saturated cyclic alkyl group, a monovalent unsaturated cyclic alkyl group, a multivalent unsaturated cyclic alkyl group, a monovalent aryl group, a monovalent aryl group with substituents, a multivalent aryl group, a multivalent aryl group with substituents, an acyl group, or an N-acyl group,
B represents oxygen, sulfur or nitrogen,
M represents

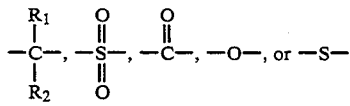

in which
$R_1$ and $R_2$ each represents hydrogen or a $C_1$-$C_4$ alkyl group,
$R_3$ represents hydrogen or a $C_1$-$C_4$ alkyl group, and
b) 0.01 to 1 wt % of a silylated acid represented by the formula $$X-[Si(CH_3)_3]_a \qquad (II)$$

in which
X represents an acidic group obtained by the removal of an acidic hydrogen atom from an acid with a $pK_a$ value of not more than 2 and
a represents an integer of from 1 to 3.

2. The composition of claim 1 in which component a) is present in an amount of from 0.1 to 2 wt %.

3. The composition of claim 2 in which component b) is present in an amount of from 0.01 to 0.1 wt %.

4. The composition of claim 1 in which component b) is present in an amount of from 0.01 to 0.1 wt %.

5. The composition of claim 1 in which the organic polyisocyanate is a diphenylmethane polyisocyanate.

6. The composition of claim 1 in which the organic polyisocyanate is a mixture of polyisocyanates of the diphenylmethane series.

7. The composition of claim 1 in which the organic polyisocyanate is a chemically modified polyisocyanate.

8. The composition of claim 1 in which component a) is selected from the group consisting of phenoxypropylene oxide and bisphenol-A polyglycidyl ether.

9. The composition of claim 8 in which component b) is selected from the group consisting of trifluoromethane sulfonic acid trimethylsilyl ester and phosphoric acid tris(trimethylsilyl ester).

10. A process for the production of a stabilized organic polisocyanate composition mixing
(a) an organic polyisocyanate with
(b) 0.01–10 wt % of an epoxide represented by the formula

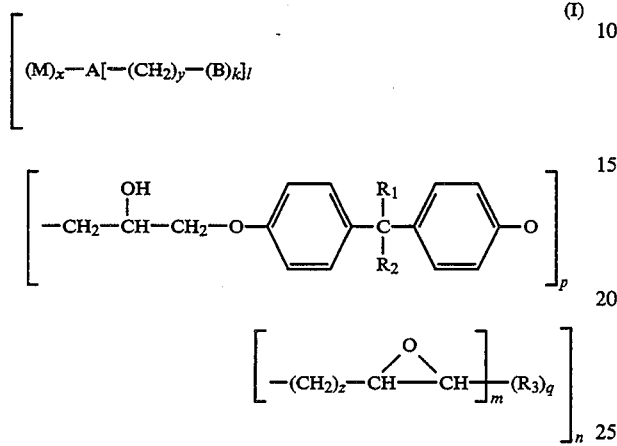
(I)

in which
x represents a number from 0 to 1,
y represents a number from 0 to 4,
z represents a number from 0 to 6,
k represents a number from 0 to 1,
l represents a number from 0 to 8,
m represents a number from 0.5 to 4,
n represents a number from 1 to 10,
p represents a number from 0 to 15,
q represents a number from 0 to 1,
A represents hydrogen, a monavalent saturated alkyl group, a multivalent saturated alkyl group, a monovalent unsaturated alkyl group, a multivalent unsaturated alkyl group, a monovalent saturated cyclic alkyl group, a multivalent saturated cyclic alkyl group, a monovalent unsaturated cyclic alkyl group, a multivalent unsaturated cyclic alkyl group, a monovalent aryl group, a monovalent aryl group with substituents, a multivalent aryl group, a multivalent aryl group with substituents, an acyl group, or an N-acyl group,
B represents oxygen, sulfur or nitrogen,
M represents

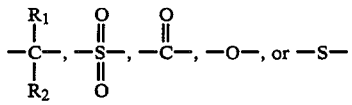

in which
$R_1$ and $R_2$ each represents hydrogen or a $C_1$–$C_4$ alkyl group,
$R_3$ represents hydrogen or a $C_1$–$C_4$ alkyl group, and
c) 0.01 to 1 wt % of a silylated acid represented by the formula $$X—[Si(CH_3)_3]_a \quad (II)$$

in which
X represents an acidic group obtained by the removal of an acidic hydrogen atom from an acid with a $PK_a$ value of not more than 2 and
a represents an integer of from 1 to 3 at a temperature of from about 20° to about 150° C.

11. The process of claim 10 in which component b) is used in an amount of from 0.1 to 2 wt % and component c) is used in an amount of from 0.01 to 0.1 wt %.

12. The process of claim 10 in which the organic polyisocyanate a) is selected from the group consisting of chemically modified polyisocyanates and mixtures of polyisocyanates of the diphenylmethane series.

13. The process of claim 10 in which the epoxide b) is selected from the group consisting of phenoxypropylene oxide and bisphenol-A polyglycidyl ether.

14. The process of claim 10 in which component c) is selected from the group consisting of trifluoromethane sulfonic acid trimethylsilyl ester and phosphoric acid tris(trimethylsilyl ester).

15. A process for the production of polyisocyanate addition products in which the polyisocyanate composition of claim 1 is reacted with an isocyanate-reactive material.

* * * * *